(12) United States Patent
Veneroni et al.

(10) Patent No.: US 9,797,528 B2
(45) Date of Patent: Oct. 24, 2017

(54) CONNECTOR WITH DOUBLE LUMEN TUBE

(71) Applicant: Fresenius Medical Care Deutschland GmbH, Bad Homburg (DE)

(72) Inventors: Alain Veneroni, Spino d'Adda (IT); Massimo Fini, Palazzo Pignano (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 539 days.

(21) Appl. No.: 14/361,801

(22) PCT Filed: Nov. 14, 2012

(86) PCT No.: PCT/EP2012/004718
§ 371 (c)(1),
(2) Date: May 30, 2014

(87) PCT Pub. No.: WO2013/079160
PCT Pub. Date: Jun. 6, 2013

(65) Prior Publication Data
US 2014/0311578 A1    Oct. 23, 2014

Related U.S. Application Data

(60) Provisional application No. 61/564,980, filed on Nov. 30, 2011.

(30) Foreign Application Priority Data

Nov. 30, 2011 (EP) .................................... 11009454

(51) Int. Cl.
*A61B 19/00* (2006.01)
*F16L 9/19* (2006.01)
(Continued)

(52) U.S. Cl.
CPC ............... *F16L 9/19* (2013.01); *A61M 39/08* (2013.01); *A61M 39/105* (2013.01);
(Continued)

(58) Field of Classification Search
CPC ........ F16L 9/19; A61M 39/08; A61M 39/105; A61M 2039/082; Y10T 156/10; Y10T 137/0318
(Continued)

(56) References Cited

U.S. PATENT DOCUMENTS 3,495,595 A    2/1970  Sopher
5,401,241 A    3/1995  Delany
(Continued)

FOREIGN PATENT DOCUMENTS

GB    1 432 105    4/1976
GB    2 307 180    5/1997
(Continued)

*Primary Examiner* — Philip R Wiest
(74) *Attorney, Agent, or Firm* — Jacobson Holman, PLLC.

(57) ABSTRACT

An assembly of a dual lumen tubing and a dual bore connector has a first flow conduit along a first lumen and a first bore, and has a second flow conduit from a second bore, via a circumferential groove and along a second lumen. The assembly can be used in connection with an extracorporeal circuit of a haemodialysis machine or an infusion set.

8 Claims, 3 Drawing Sheets

(51) Int. Cl.
*A61M 39/08* (2006.01)
*A61M 39/10* (2006.01)

(52) U.S. Cl.
CPC .. *A61M 2039/082* (2013.01); *Y10T 137/0318* (2015.04); *Y10T 156/10* (2015.01)

(58) Field of Classification Search
USPC ............................. 604/4.01–6.16, 403–416
See application file for complete search history.

(56) References Cited

U.S. PATENT DOCUMENTS

| | | | |
|---|---|---|---|
| 5,868,717 A | 2/1999 | Prosl | |
| 2006/0270962 A1* | 11/2006 | McGuckin | A61M 1/285 604/6.16 |
| 2007/0088218 A1 | 4/2007 | McIntyre et al. | |
| 2008/0011368 A1* | 1/2008 | Singh | A61M 1/0088 137/565.01 |
| 2011/0315147 A1 | 12/2011 | Wood et al. | |

FOREIGN PATENT DOCUMENTS

| | | |
|---|---|---|
| WO | WO 87/07159 | 12/1987 |
| WO | WO 2011/054693 | 5/2011 |
| WO | WO 2012/010322 | 1/2012 |

* cited by examiner

CONNECTOR WITH DOUBLE LUMEN TUBE

CROSS-REFERENCE TO RELATED APPLICATION

This application claims the benefit of priority to U.S. Provisional Application for Patent No. 61/554,980, filed Nov. 30, 2011.

BACKGROUND OF THE INVENTION

1. Field of Invention

The present invention relates to a double lumen tubing set and connector. This tubing set is intended for use with infusion bags or vials. In particular the tubing set is intended to be used with haemodialysis machines or an infusion set.

2. Description of the Prior Art

In haemodialysis treatments which require an extracorporeal circulation it is often necessary to administer different drugs or therapeutic substances to the patient. The presence of the tubing set advantageously makes it possible to avoid the administering of the drug taking place through puncture carried out directly on the patient himself.

During the haemodialysis treatments it often becomes necessary to administer different drugs or therapeutic substances, like iron, heparin, erythropoietin, vitamins and antibiotics. The infusion of such substances in the extracorporeal circuit is currently carried out through conventional syringes. The substance is drawn from a vial or ampoul in which it is supplied by the manufacturer and is then injected into a special puncturable access point provided along the tubing set. Thus there is a double transfer of the substance: firstly from the vial to the syringe and then from the syringe to the circuit. Such an operation therefore requires the use of disposable materials, such as the syringe and the respective needle, just to transfer the substance from the vial to the tubing set. Moreover, the use of needles always carries the risk of the service staff being pricked. In case the drug is supplied in ampouls, these have to be broken with risk of injuries (sharp edges) or to suck possible glass fragments into the syringe.

Finally, some of the quoted substances need to be administered slowly, over a few minutes. Therefore it can easily be understood how the administering of various substances to more than one patient represents a considerable workload for the nursing staff responsible for the treatment.

WO 2011/054693 discloses a tubing set having a gate for the connection of vials to an extra-corporeal circuit of a haemodialysis machine.

WO 87/07159 discloses a medical fluid administration set which is intended for infusions related to an intravenous therapy; such set is not suitable for use in cooperation with a haemodialysis machine.

GB 1432105 discloses a medical drain comprising an elongate tube having a central first lumen and a peripheral outer wall, a second lumen integral with and lying within the peripheral outer wall in spaced parallel relation to the central first lumen.

U.S. Pat. No. 3,495,595 discloses a medico-surgical tube comprising a double lumen tube.

U.S. Pat. No. 5,401,241 discloses a duodenal intubation catheter comprising a double lumen tube.

U.S. Pat. No. 5,868,717 discloses a dual-lumen catheter and method of use.

Problem of the Invention

Conventional tubing sets for infusion comprise a single lumen line connecting a vial and a drip chamber. The single lumen line serves two functions. Firstly, it acts as a delivery lumen, suitable for delivering the drug from the vial to the drip chamber. And secondly, it acts as a vent lumen, suitable for providing air inside the vial in order to replace the delivered drug. In other words, the liquid infusion flows down to the drip chamber, while air returns through the same line to vent the vial for pressure compensation. This countercurrent flow may lead to an unsteady flow of the medicament to the drip chamber. It is one task of the present invention to provide a steady flow of a liquid medicament from a vial to a patient infusion line or to an extracorporeal circuit of a haemodialysis machine.

Alternatively, two separate lumen may be used to achieve a steady flow of medicament and air. While single lumen tubes are readily available, an assembly of two tubes may in some cases be time-consuming and the correct connection of each tube has to be assured. In some cases two tubes cannot be connected due to spatial constrains in the design of a haemodialysis machine.

Dual or multi lumen tubes have two or more lumen running parallel. Dual lumen tubing sets are known from prior art. They are frequently used for a multitude of applications. In one typical embodiment a dual lumen tubing comprises two parallel lumen attached to each other having a cross section with a shape of a figure 'eight' or two connected semicircles forming an overall circular shape.

One drawback of conventional dual lumen tubing is that the assembly requires high precision. At both ends of the tubing each lumen has to be connected to its respective port. Furthermore, a high angular precision is necessary in order to achieve a tight connection between the tubing and a connector. Even a mirror axial rotation of the tube may lead to an insufficient connection of one or both lumen. A rotation of 180° will result in a mix-up of both lumen.

Tubing sets for use in infusion and/or haemodialysis are commonly single use items, which will be disposed of after use. As the price for disposable articles is typically low such items require low cost manufacturing. This is normally achieved by a highly automated production process. It is economically advantageous to limit the number of manual production steps or even completely eliminate them from the production process. Thus, it is another task of the present invention to provide a tubing set which can be manufactured in a highly automated production process.

SUMMARY OF THE INVENTION

In one aspect, the invention relates to a dual lumen tubing comprising a first circular lumen and a second lumen wherein said first lumen has a circular inner cross section with radius r1 and an outer circular cross section with radius r2 and wherein the second lumen is located in the wall of the tubing having a diameter d3 with d3<(r2−r1).

In another aspect, the invention relates to a dual bore connector comprising a first bore, two circular contact surfaces and a circumferential groove between the inner radius r1 and the outer radius r2 and embedding the second bore. In yet another embodiment, the dual bore connector may, optionally, comprise an inner cylindrical connection means with an outer radius r1 and/or an outer cylindrical connection means with an inner radius r2.

In yet another aspect, the invention relates to an assembly of a dual lumen tubing as described above and a dual bore connector as described above having a first flow conduit along the first lumen and the first bore, and having a second flow conduit from the second bore, via the circumferential groove and along the second lumen.

Such an assembly may be used in connection with an extracorporeal circuit of a haemodialysis machine or an infusion set.

The invention is also directed to a process for manufacture of an assembly as described above comprising the step of glueing, and, optionally, simultaneously or consecutively blowing a gas through the second bore, via the circumferential groove and along the second lumen.

BRIEF DESCRIPTION OF THE DRAWINGS

The characteristics and the further advantages of the present invention shall become clear from the following description of some embodiments, given for indicating and not limiting purposes with reference to the attached drawings.

DETAILED DESCRIPTION OF THE PREFERRED EMBODIMENTS

Figure 1:
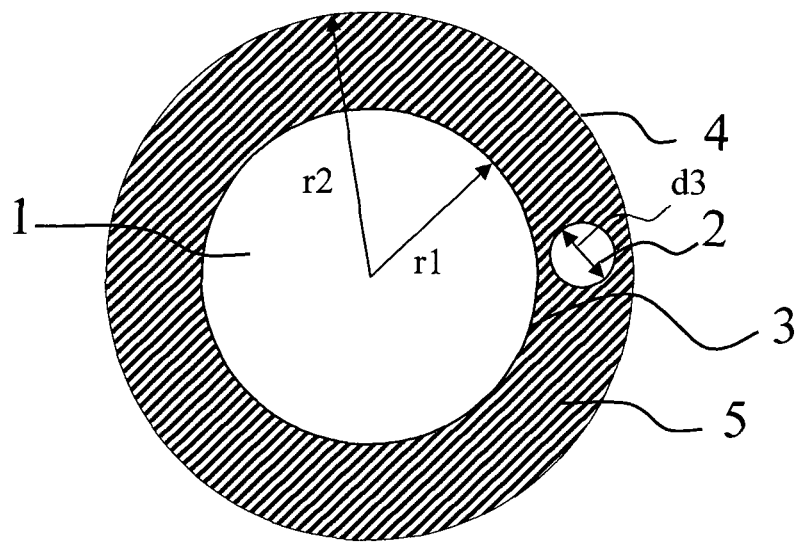
FIG. 1 schematically represents a cross sectional view of a dual lumen tubing according to the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The problems described above are solved by the present invention by providing a dual lumen line having two separate lumina comprising a first circular lumen (1) and a second lumen (2) wherein said first lumen (1) has a circular inner (3) cross section and a circular outer cross section (4) and wherein the second lumen is located in the wall (5) of the tubing and wherein this double lumen tube is connected to a dual bore connector comprising a first bore (6) and a second bore (10) and having a circumferential groove (9) around the first bore (6) embedding the second bore (10).

The two lumina of the dual lumen tube are connected to the two bores of the dual bore connector facilitating two flow conduits. A first conduit is formed by the circular lumen (1) and the first bore (6). The second conduit is formed by the second lumen (2) and the second bore (10) via the circumferential groove (9). A permanent flow connection between the second lumen (2) and the second bore (10) is facilitated by the circumferential groove (9), which is independent of an axial rotation of the dual lumen tube during assembly or use.

In the description of the present invention the term "dual lumen tube" refers to a tube having two lumina running parallel and with one lumen embedded in the wall of a first lumen. More specifically, the term "dual lumen tube" refers to a tube comprising a first circular lumen (1) and a second lumen (2) wherein said first lumen (1) has a circular inner cross section (3) with radius r1 and an outer circular cross section (4) with radius r2 and wherein the second lumen is located in the wall (5) of the tubing having a diameter d3 with d3<(r2−r1).

In the description of the present invention the term "dual bore connector" refers to a connecting means having two bores and a circumferential groove around a first bore and embedding the second bore. More specifically, the term "dual bore connector" refers to a connecting means (11) comprising
a first bore (6),
a circular contact surface (12) with an inner radius r1 and a circular contact surface (13) with an outer radius r2 surrounding said first bore (6), and
a circumferential groove (9) between the inner radius r1 and the outer radius r2 and embedding the second bore (10).

In the description of the present invention the term "assembly" refers to a combination of a "dual lumen tube" and a "dual bore connector" as defined above.

Embodiments of the present invention will be disclosed in detail, with specific reference to FIGS. 1-6. In such embodiments the liquid medicament flows—either by gravity or pressure difference, e.g., generated by a pump or pneumatic pressure—from a fluid reservoir (e.g. a vial or an IV bag) through the delivery port (10) via the circumferential groove (9) to the delivery lumen (2). In return, air flows through the vent lumen (1) and the bore (6) to the fluid reservoir.

One aspect of the invention is depicted in FIG. 1 and relates to a dual lumen tubing comprising a first circular lumen (1) and a second lumen (2) in the wall (5) of the tubing forming said first lumen (1) and having a circular inner (3) and a circular outer cross section (4).

Figure 2:
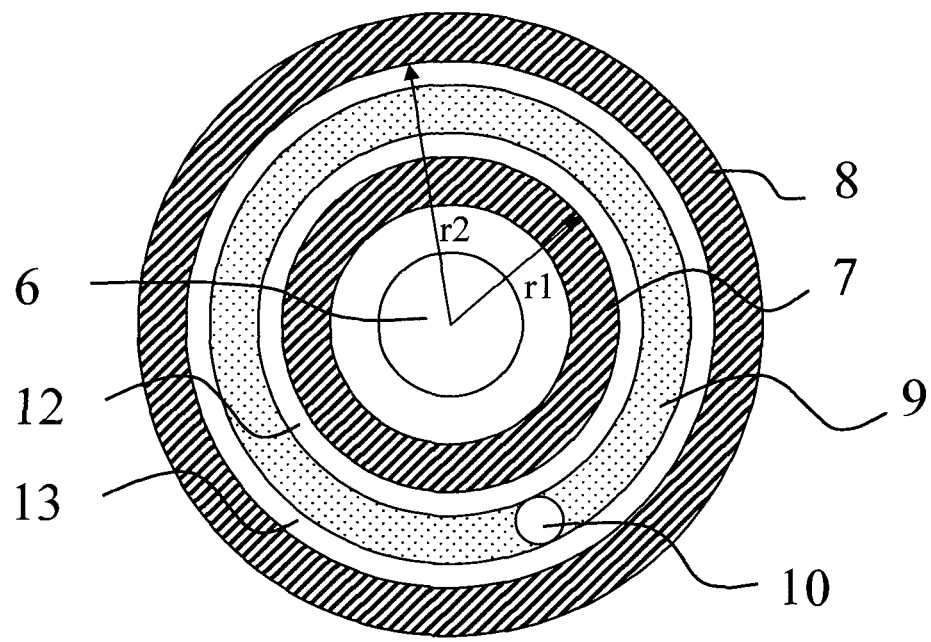
FIG. 2 schematically represents a cross sectional view of a dual bore connector according to the present invention.

One further aspect of the present invention is depicted in FIG. 2 and relates to a dual bore connector comprising
a first bore (6),
a circular contact surface (12) with an inner radius r1 and a circular contact surface (13) with an outer radius r2 surrounding said first bore (6), and
a circumferential groove (9) between the inner radius r1 and the outer radius r2 and embedding the second bore (10).

Figure 3:
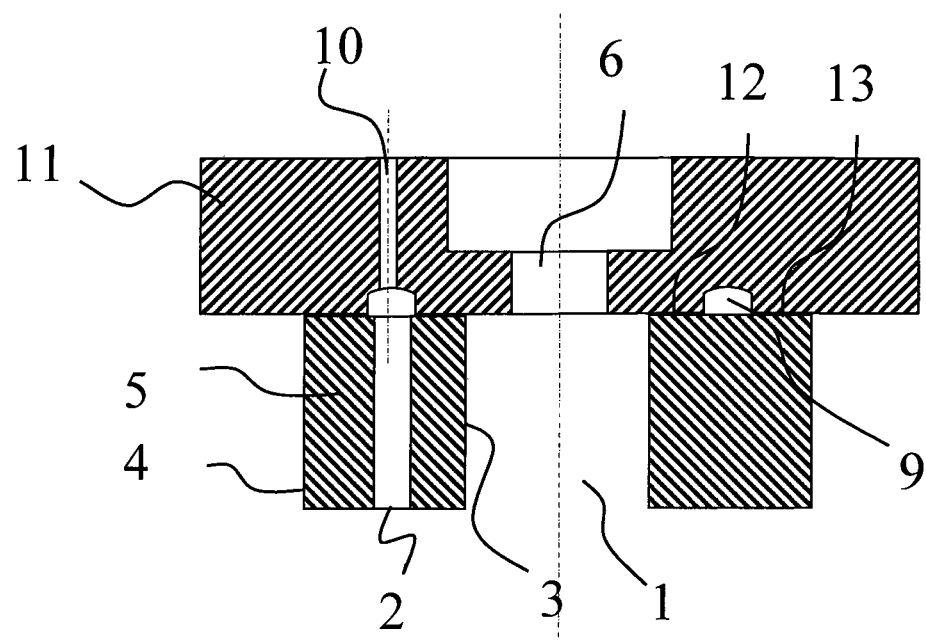
FIG. 3 schematically represents a cross sectional view of an assembly of a dual lumen tube and a dual bore connector according to the present invention.

One embodiment of the present invention is depicted in FIG. 3 and relates to an assembly of a dual lumen tube (1-5) and a dual bore connector (6-13) comprising a first bore (6), a circular contact surface (12) with an inner radius r1 and a circular contact surface (13) with an outer radius r2 surrounding said first bore (6), a circumferential groove (9) between the inner radius r1 and the outer radius r2 and embedding the second bore (10), and a dual lumen tube being attached to the contact surfaces (12) and (13) of the dual bore connector. The dual lumen tube can be attached to the contact surfaces (12) and (13) of the dual bore connector by means of, e.g., welding or glueing.

In further embodiments of the present invention the dual bore connector optionally comprises one or two circular connection means (7) and (8) having a cylindrical or tubular shape. A dual lumen tube as defined above can be attached to the dual bore connector by fitting it onto the tubular connection means (7) and (8). Examples of further embodiments comprise one or two circular connection means (7) and/or (8) are depicted in FIGS. 4-6.

Figure 4:
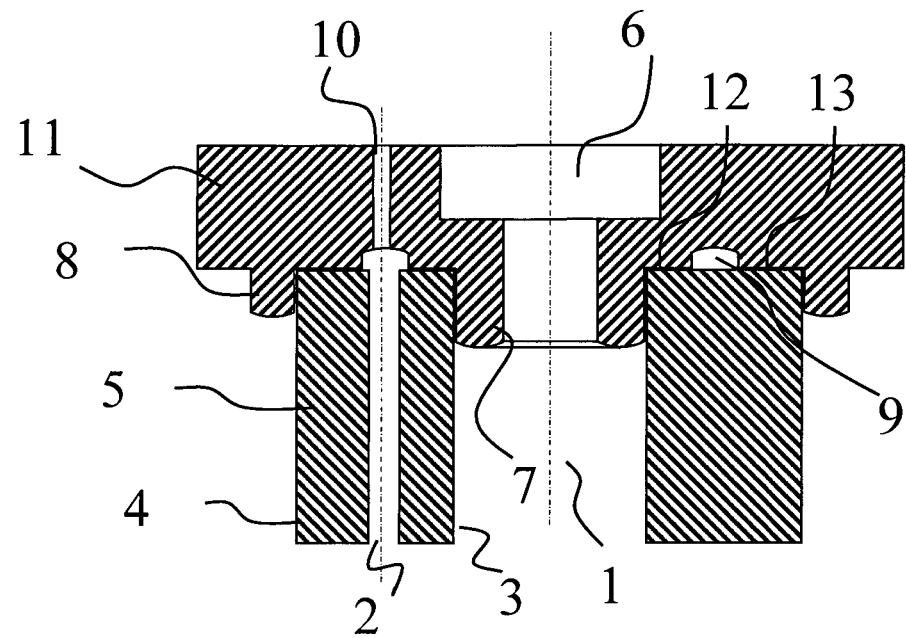
FIGS. 4-6 schematically represent cross sectional views of assemblies of a dual lumen tube and a dual bore connector according to further embodiments of the present invention.

One further embodiment of the present invention is depicted in FIG. 4 and relates to an assembly of a dual lumen tube (1-5) and a dual bore connector (6-13). The assembly comprises a dual bore connector having two cylindrical connection means [(7) and (8)] around a first bore (6) and having two contact surfaces [(12) and (13)], and a circumferential groove (9) embedding the second bore (10) in between the two cylindrical connection means [(7) and (8)]. The dual lumen tube (1-5) is attached to the dual bore connector (6-13) by fitting it in between the two cylindrical connection means [(7) and (8)], and, optionally, glueing or welding it to the contact surfaces (12) and (13).

Figure 5:
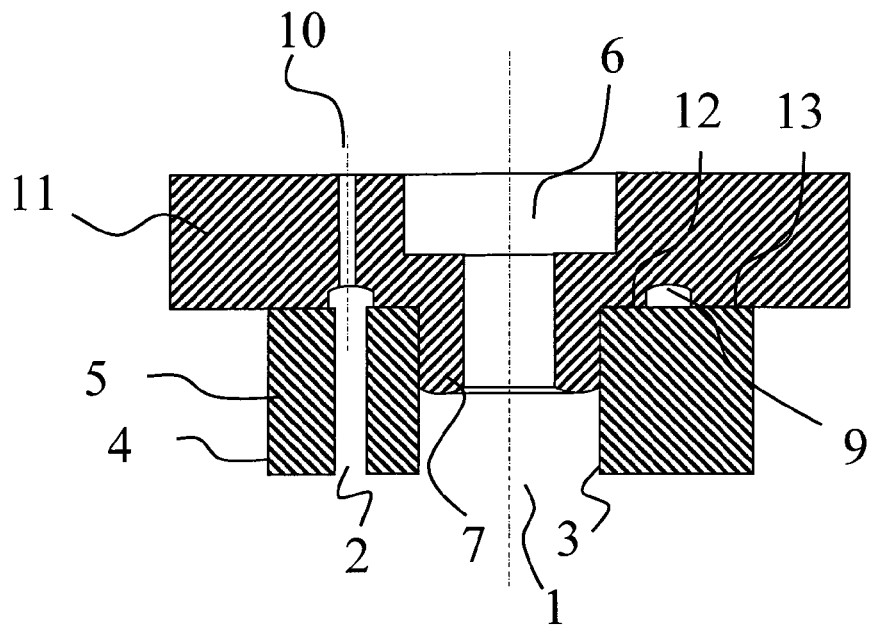

One further embodiment of the present invention is depicted in FIG. 5 and relates to an assembly of a dual lumen tube (1-5) and a dual bore connector (6-13). The assembly comprises a dual bore connector having one cylindrical connection means (7) around a first bore (6) and having two contact surfaces (12) and (13), and a circumferential groove (9) embedding the second bore (10) around the cylindrical connection means (7). The dual lumen tube (1-5) is attached to the dual bore connector (6-13) by fitting the first lumen (1) onto the cylindrical connection means (7), and, optionally, glueing or welding it to the contact surfaces (12) and (13).

Figure 6:
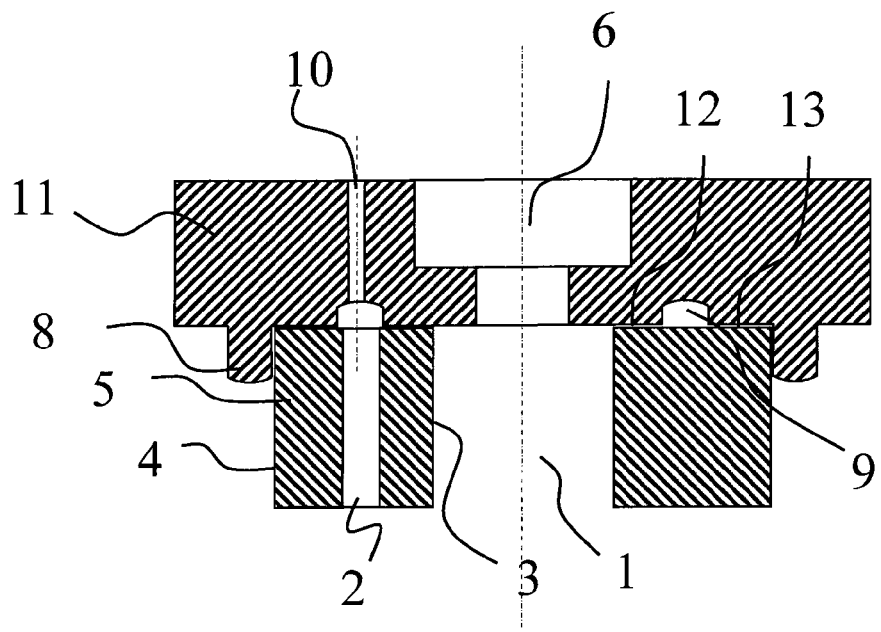

One further embodiment of the present invention is depicted in FIG. 6 and relates to an assembly of a dual lumen tube (1-5) and a dual bore connector (6-13). The assembly comprises a dual bore connector having one cylindrical connection means (8) around a first bore (6) and having two contact surfaces (12) and (13), and a circumferential groove (9) embedding the second bore (10) in between the first bore (6) and the cylindrical connection means (8). The dual lumen tube (1-5) is attached to the dual bore connector (6-13) by fitting it into the cylindrical connection means (8), and, optionally, glueing or welding it to the contact surfaces (12) and (13).

In a second embodiment of the present invention, the allocation of the two lumen (1) and (2) is swapped. Again, reference is made to FIGS. 1-6. In such a second embodiment the liquid medicament flows—either by gravity or pressure difference, e.g., generated by a pump or pneumatic pressure—from a fluid reservoir (e.g. a vial or an intravenous infusion bag) through the delivery port (6) to the delivery lumen (1). In return, air flows through the vent lumen (2) via the circumferential groove (9) and the bore (10) to the fluid reservoir.

Dual lumen tubes can be made from one or a combination of different materials. Without limitation such materials include, e.g., polyamide (Nylon), polyurethane, polyethylene (HDPE, LDPE or LLDPE), polypropylene, PVC, PTFE (Teflon), synthetic or natural rubbers, silicone, stainless steel and other metal material or combinations thereof.

Dual lumen tubes are obtainable using processes known to those skilled in the art. Without limitation such processes include, e.g., extrusion, welding, winding rotary piercing, drawing over a mandrel and sewing. A preferred process is extrusion.

The dual bore connector can be made from one or a combination of different materials. Without limitation such materials include, e. g., nylon, polyesters, polyurethane, polypropylene, polystyrene, polyethylene (HDPE, LDPE or LLDPE), polycarbonate, ABS, PVC, PTFE (Teflon), styrene-acrylonitrile resin stainless steel and other metal material or combinations thereof.

The dual bore connector can be manufactured by, e.g., injection moulding, turning or milling.

The dual lumen tube as described above is attached to the dual bore connector.

The dual lumen tube can be attached to the connector by any means of fastening known to those skilled in the art. Without limitation, examples for means of fastening are ferrules, clamps or tube clips. The tube may in addition or alternatively be fastened to the connector by welding or by use of an adhesive or glue. The adhesives can be solvent-type glues, synthetic monomer glues or synthetic polymer glues.

In one preferred embodiment the tube is attached to the connector by glueing. During the process of glueing a gas is preferably blown through the lumen (1) and/or (2) or through the ports (6) and/or (10) of the connector to prevent glue from blocking the fluid flow paths of the assembly. Without limitation the gas may include nitrogen, oxygen, noble gases or air. Air is the preferred gas.

In another preferred embodiment the tube is attached to the connector by mechanical interference and glueing. (see FIG. 4) The tube is attached to the connector by mechanical interference with the cylindrical connection means (7) and glueing the tube to the cylindrical connection means (8). Glue is applied to the outer surface (4) of the tube, while no glue is applied to the front end and the inner surface (3) of the tube.

Examples for solvent-type glues are polystyrene cement/butanone or dichloromethane, which by welding bond the material together. Examples for synthetic monomer glues are acrylonitrile, cyanoacrylate ("Superglue"), acrylic or resorcinol glue. Examples for synthetic polymer glues are epoxy resins, ethylene-vinyl acetate (a hot-melt glue), phenol formaldehyde resin, polyamide, polyester resins, polyethylene (a hot-melt glue), polypropylene, polysulfides, polyurethane, polyvinyl acetate (PVA), polyvinyl alcohol, polyvinyl chloride (PVC), polyvinyl chloride emulsion (PVCE), polyvinyl pyrrolidone (PVP), rubber cement, silicones and styrene acrylic copolymer.

The invention being thus described, it will be apparent that the same may be varied in many ways Such variations are not to be regarded as a departure from the spirit and scope of the invention, and all such modifications as would be recognized by one skilled in the art are intended to be included within the scope of the following claims.

What is claimed is:

1. A dual bore connector comprising
   a first bore associated with a first lumen, and a second bore associated with a second lumen,
   a circular contact surface having an inner radius r1, and a circular contact surface having an outer radius r2 surrounding the first bore, and
   a circumferential groove between the inner radius r1 and the outer radius r2 and embedding the second bore,
   with the circumferential groove providing for fluid communication between the second lumen and the second bore.

2. The dual bore connector according to claim 1, further comprising at least one of
   an inner cylindrical connection element having an outer radius substantially equal to the inner radius r1 of the circular contact surface,
   and an outer cylindrical connection element having an inner radius substantially equal to the outer radius r2 of the circular contact surface.

3. The dual bore connector according to claim 1, wherein the fluid communication between the second lumen and the second bore is independent of any axial rotation of the second lumen relative to the second bore.

4. An assembly comprising:
   a dual bore connector; and
   a dual lumen tubing having a first lumen and a second lumen,
   the dual bore connector having a first bore associated with the first lumen of the tubing, and a second bore associated with the second lumen of the tubing, a circular contact surface having an inner radius r1, and a circular contact surface having an outer radius r2 surrounding the first bore, and a circumferential groove between the inner radius r1 and the outer radius r2 and embedding the second bore, with the circumferential groove providing for fluid communication between the second lumen and the second bore, the first lumen having a circular inner cross section with the radius r1 and an outer circular cross section with the radius r2, and with the second lumen being located in a wall of the tubing and having a diameter d3, with $d3<(r2-r1)$.

5. The assembly according to claim 4, wherein the assembly provides a first flow conduit along the first lumen and the first bore, and a second flow conduit from the second bore, via the circumferential groove, and along the second lumen.

6. A process for manufacture of an assembly according to claim 4, said process comprising a step of securing the dual lumen tubing to the dual bore connector with a glue.

7. The process according to claim 6, further comprising a step of blowing a gas through the second lumen or the second bore.

8. A connectable system comprising:
an extracorporeal circuit of a haemodialysis machine or an infusion set; and
an assembly according to claim 4.

* * * * *